(12) United States Patent
Ischia et al.

(10) Patent No.: US 12,208,028 B2
(45) Date of Patent: Jan. 28, 2025

(54) STENT INSERTION APPARATUS AND METHODS

(71) Applicant: JiffyStent Pty Ltd, East Melbourne (AU)

(72) Inventors: Joseph Ischia, East Melbourne (AU); Donald Fry, East Melbourne (AU)

(73) Assignee: JIFFYSTENT PTY LTD, East Melbourne (AU)

( * ) Notice: Subject to any disclaimer, the term of this patent is extended or adjusted under 35 U.S.C. 154(b) by 0 days.

(21) Appl. No.: 18/392,182

(22) Filed: Dec. 21, 2023

(65) Prior Publication Data

US 2024/0216156 A1   Jul. 4, 2024

Related U.S. Application Data

(63) Continuation of application No. PCT/AU2022/051599, filed on Dec. 29, 2022.

(30) Foreign Application Priority Data

Jan. 10, 2022   (AU) ................. 2022900040

(51) Int. Cl.
*A61F 2/95*   (2013.01)
*A61F 2/04*   (2013.01)
(Continued)

(52) U.S. Cl.
CPC ............ *A61F 2/9517* (2020.05); *A61F 2/966* (2013.01); *A61F 2002/048* (2013.01);
(Continued)

(58) Field of Classification Search
CPC .......... A61F 2/95; A61F 2/9517; A61F 2/954; A61F 2/962; A61F 2/966; A61M 2025/09116; A61M 2025/09125
See application file for complete search history.

(56) References Cited

U.S. PATENT DOCUMENTS 6,852,116 B2   2/2005   Leonhardt et al.
8,684,913 B2   4/2014   Frassica et al.
(Continued)

FOREIGN PATENT DOCUMENTS

EP           1755727 B1    2/2007
WO      WO 2010/017006 A1  2/2010
(Continued)

OTHER PUBLICATIONS

International Search Report for PCT/AU2022/051599 dated Feb. 27, 2023.
(Continued)

*Primary Examiner* — Todd J Scherbel
(74) *Attorney, Agent, or Firm* — FROST BROWN TODD LLP

(57) ABSTRACT

The present invention relates generally to an apparatus for placing a stent at a desired location within the human body. In particular, but not exclusively, the apparatus is configured to place a stent within the ureter or other passage or space within the human body. The invention may be embodied as an apparatus for inserting a stent into a bodily structure of a subject, the apparatus comprising: a stent guide wire, a first moving means configured to move the stent guide wire toward a bodily structure of a subject, a stent pusher disposed about the stent guide wire, and a second moving means configured to move the stent pusher independently of and relative to the stent guide wire.

29 Claims, 5 Drawing Sheets

(51) Int. Cl.
*A61F 2/966* (2013.01)
*A61M 25/09* (2006.01)

(52) U.S. Cl.
CPC .............. *A61M 2025/09116* (2013.01); *A61M 2025/09125* (2013.01); *A61M 2025/09183* (2013.01)

(56) References Cited

U.S. PATENT DOCUMENTS

| | | |
|---|---|---|
| 8,968,380 B2 | 3/2015 | Nimgaard |
| 10,201,351 B2 | 2/2019 | Castleberry et al. |
| 10,779,978 B2 | 9/2020 | Maier et al. |
| 11,026,821 B2 | 6/2021 | Wübbeling et al. |
| 11,241,324 B2 * | 2/2022 | Halbert .................... A61F 2/97 |
| 2008/0039893 A1 | 2/2008 | McLean et al. |
| 2012/0316393 A1 | 12/2012 | Frassica et al. |
| 2017/0333238 A1 * | 11/2017 | Dooley .................... A61F 2/95 |
| 2019/0262155 A1 | 8/2019 | Lam et al. |
| 2020/0360164 A1 | 11/2020 | Janku et al. |
| 2021/0052382 A1 | 2/2021 | Duffy et al. |
| 2021/0052403 A1 | 2/2021 | Chu et al. |
| 2021/0322165 A1 * | 10/2021 | Montgomery ........ A61F 2/2427 |

FOREIGN PATENT DOCUMENTS

| | | |
|---|---|---|
| WO | WO 2017/161311 A1 | 9/2017 |
| WO | WO 2019/053507 A1 | 3/2019 |
| WO | WO 2019/053508 A1 | 3/2019 |
| WO | WO 2021/166156 A1 | 8/2021 |

OTHER PUBLICATIONS

Written Opinion of the International Search Authority for PCT/AU2022/051599 dated Feb. 27, 2023.

* cited by examiner

STENT INSERTION APPARATUS AND METHODS

FIELD OF THE INVENTION

This application is a continuation of PCT/AU2022/051599, filed Dec. 29, 2022, entitled Stent Insertion Apparatus and Methods, which claims priority to AU202290040, filed Jan. 10, 2022, the disclosures of which are each incorporated by reference herein.

The present invention relates generally to an apparatus for placing a stent at a desired location within the human body. In particular, but not exclusively, the apparatus is configured to place a stent within the ureter or other passage or space within the human body.

BACKGROUND TO THE INVENTION

A stent is a tubular structure placed into the human body to return a passage to patency, thereby allowing for a bodily fluid to flow therethrough. In other applications, a stent is used to encourage cross-sectional expansion of a passage within the body. In yet a further application a stent may be used prophylactically to prevent blockage.

A common site of stent placement is within the ureter. The ureter must remain patent to allow urine to drain from kidney and into the bladder. Obstruction of the ureter often manifests symptoms including pain, fever, and vomiting. Ongoing blockage can lead to infection and serious renal damage.

The ureter may become blocked or partially occluded by an internal obstruction such as a ureteric stone. Alternatively an external mass such as a tumour, lymph node or fibrosis may compress the ureter. In other circumstances the ureter becomes kinked or the walls thickened. A ureteric stent may be placed to prevent blockage caused by a procedure, such as kidney stone lithotripsy.

A ureteric stent generally takes the form of a hollow tube, fabricated from a flexible plastic. The length of a stent used for an adult subject is typically between about 45 cm in length, having a straight section of between about 22 cm to 30 cm in length, and coiled sections at each terminus. The coiled sections retain the stent in place. The coil at one terminus locates in the renal pelvis and coil at the other terminus locates in the bladder.

Ureteric stent insertion is often performed under general anaesthesia. Cystoscopy is performed first to inject contrast agent into the ureter. Real time images are obtained by fluoroscopy to outline the urinary collection system from the kidney to the bladder. A guide wire is inserted into the ureter and the end advanced into the renal pelvis. The stent is placed over the wire, and kept generally linear by the wire as it is advanced toward the renal pelvis using a pusher. Once the terminus of the stent is located in the pelvis the guide wire is withdrawn thereby allowing each end of the stent to assume its normal coiled configuration.

Existing methods of ureteric stent insertion present a number of problems.

A significant problem is that the insertion of a ureteric stent cannot be carried out in an emergency department or in a general clinic setting given to the need for a specialist urologist and specialised equipment normally only available in an operating room. Ureteric stent insertion is generally beyond the skill of a non-specialist medical practitioner. Expertise and experience is firstly required to operate the specialised equipment in the context of a complex multi-step process. Further expertise and experience is required to ensure that the stent is advanced sufficiently far such that the distal coiled portion locates in the renal pelvis, but not so far that the guide wire or stent injures any renal tissue or the stent is completely lost into the ureter. Accordingly, stent insertion is often delayed by up to an entire day given the need to assemble the required specialist team, including a urologist, and arrange for access to an imaging suite. In that time, the subject may be in significant pain and at risk of renal damage arising from the ureteric blockage.

A further problem is that even in expert hands, a ureteric stent can be difficult to properly insert. A high level of manual dexterity is required to finely manipulate the guide wire and the stent pusher. Even with fluoroscopic guidance it is possible for the subject to suffer some renal injury due to the wire or stent being advance too far into the kidney.

It is an aspect of the present invention to provide an improvement to prior art apparatus and methods for inserting a stent, and particularly a ureteric stent. It is a further aspect of the present invention to provide a useful alternative to prior art apparatus and methods for inserting a stent, and particularly a ureteric stent.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, but not necessarily the broadest aspect, the present invention provides an apparatus for inserting a stent into a bodily structure of a subject, the apparatus comprising:
 a stent guide wire,
 a first moving means configured to move the stent guide wire toward a bodily structure of a subject,
 a stent pusher disposed about the stent guide wire, and
 a second moving means configured to move the stent pusher independently of and relative to the stent guide wire.

In one embodiment of the first aspect, the apparatus is configured such that the stent guide wire and the stent pusher are movable together in a mutually dependent manner together.

In one embodiment of the first aspect, the first and/or second moving means is/are configured such that the stent guide wire and the stent pusher are movable together in a mutually dependent manner together.

In one embodiment of the first aspect, the apparatus is configured to alternately (i) move the stent pusher independently of and relative to the stent guide wire, and (ii) move the stent guide wire and the stent pusher in a mutually dependent manner.

In one embodiment of the first aspect, the first and/or second moving means is/are configured to alternately (i) move the stent pusher independently of and relative to the stent guide wire, and (ii) move the stent guide wire and the stent pusher in a mutually dependent manner.

In one embodiment of the first aspect, the apparatus comprises a mechanism configured to alternately lock and unlock the first and second moving means to and from each other such that alternately (i) the stent pusher is movable independently of and relative to the stent guide wire, and (ii) the stent guide wire and the stent pusher are movable in a mutually dependent manner.

In one embodiment of the first aspect, the first and second moving means are independently lockable so as to prevent movement in a direction.

In one embodiment of the first aspect, the first and/or second moving means is/are movable, a movement of the first moving means causes movement of the stent guide wire toward the bodily structure and a movement of the second moving means causes movement of the stent pusher along the stent guide wire.

In one embodiment of the first aspect, the apparatus comprises a mechanism configured to alternately lock and unlock the first and second moving means to and from each other such that alternately (i) the stent pusher is movable independently of and relative to the stent guide wire, and (ii) the stent guide wire and the stent pusher are movable in a mutually dependent manner, and the mechanism when unlocked allows the first and second moving means to move independently of each other and when locked prevents the first and second moving means from moving independently of each other.

In one embodiment of the first aspect, the first and/or second moving means is/are rotationally movable.

In one embodiment of the first aspect, the first and/or second moving means is/are rotationally movable about a rotational axis, and the first and/or second moving means have an outwardly facing surface surrounding the rotational axis, and the stent guide wire and/or stent pusher are wound onto the outwardly facing surface of the first and/or second moving means.

In one embodiment of the first aspect, the first and/or second moving means is/are a structure having a circular cross-section and stent guide wire and/or stent pusher are wound onto the outside of the structure.

In one embodiment of the first aspect, the structure having a circular cross-section is a wheel, a spool, a reel, a bobbin, a drum, or a functional equivalent thereof.

In one embodiment of the first aspect, the rotational axes of the first and second moving means are coincident.

In one embodiment of the first aspect, the apparatus is configured such that the first and/or second moving means is/are movable by hand or by a mechanism comprising a motor, a biasing means, or a spring.

In one embodiment of the first aspect, the apparatus is configured to limit the insertion distance of the stent guide wire and/or the stent pusher movable by the first and/or second moving means.

In one embodiment of the first aspect, the apparatus is configured such that the limit to the insertion distance of the stent guide wire and/or the stent pusher movable by the first and/or second moving means is adjustable.

In one embodiment of the first aspect, the apparatus comprises a stop member or a mechanical mechanism configured to limit the insertion distance of the stent guide wire and/or the stent pusher, the stop member or the mechanical mechanism configured to limit the movement of the first and/or second moving means.

In one embodiment of the first aspect, the apparatus comprises an output port through which the stent guide wire and the stent pass.

In one embodiment of the first aspect, wherein the output port communicates with an elongate structure through which the stent guide wire and the stent pass.

In one embodiment of the first aspect, the elongate structure is configured to be introduced into the body of a subject via a natural body opening or an artificially created body opening.

In one embodiment of the first aspect, the elongate structure is configured to be passed through the male or female urethra and into the bladder.

In one embodiment of the first aspect, the elongate structure comprises an electronic optical imaging device and an illumination device configured to illuminate the field covered by the imaging device.

In one embodiment of the first aspect, the apparatus comprises a wired or wireless interface configured to transmit an image-encoding signal from the imaging device to an electronic device comprising a visual display screen.

In one embodiment of the first aspect, the electronic device comprising a visual display screen is separate to or not integral with the apparatus.

In one embodiment of the first aspect, the electronic device comprising a visual display screen is a mobile device, a smart phone, a tablet computer, a lap top computer or a desktop computer.

In one embodiment of the first aspect, the mobile device, the smart phone, tablet computer, lap top computer or desktop computer comprises in stored memory software instructions to receive and decode an image-encoding signal from the imaging device and display the encoded image on the electronic device comprising a visual display screen.

In one embodiment of the first aspect, the apparatus comprises a stent disposed about the guide wire and in operable association with the stent pusher.

In one embodiment of the first aspect, the stent is configured to be placed within a fluid conducting vessel of the body.

In one embodiment of the first aspect, the fluid conducting body is a ureter.

In one embodiment of the first aspect, the stent comprises a portion that is biased toward a non-linear conformation with the guide wire maintaining a linear conformation of the portion, and withdrawal of the guide wire from the stent allows the portion to assume a non-linear conformation.

In one embodiment of the first aspect, the stent is a double-J ureteric stent.

In one embodiment of the first aspect, the apparatus comprises a housing.

In one embodiment of the first aspect, the housing provides a handle or a gripping surface.

In one embodiment of the first aspect, the housing provides a retainer to retain a mobile device.

In a second aspect, the present invention provides a method for inserting a stent into a bodily structure of a subject, the method comprising providing the apparatus of any embodiment of the first aspect, introducing the stent guide wire and stent into the body of a subject, operation of the first moving means to move the stent guide wire until the distal terminus is located within or about a bodily structure of the subject in need of stenting, and operation of the second moving means to move the stent pusher independently of and relative to the stent guide wire so as to push the stent until the distal terminus is located within or about the bodily structure in need of stenting.

In a third aspect, the present invention provides a method for inserting a stent into a bodily structure of a subject, the method comprising providing the apparatus of any embodiment of the first aspect configured such that the stent guide wire and the stent pusher are movable together in a mutually dependent manner together, disposing a stent about the stent guide wire, introducing the stent guide wire and stent into the body of a subject, operation of the first moving means to move the stent guide wire toward a bodily structure of the of the subject in need of stenting until the distal terminus is located within or about a bodily structure of a subject in need of stenting, and operation of the second moving means to move the stent pusher independently of and relative to the stent guide wire so as to push the stent until the distal terminus is located within or about the bodily structure in need of stenting.

In one embodiment of the third aspect, the method comprises operation of the first moving means so as to withdraw the stent guide wire from the stent while allowing the stent to remain within or about the bodily structure in need of stenting.

BRIEF DESCRIPTION OF THE FIGURES

Unless otherwise indicated herein, features of the drawings labelled with the same numeral are taken to be the same features, or at least functionally similar features, when used across different drawings.

Figure 1:
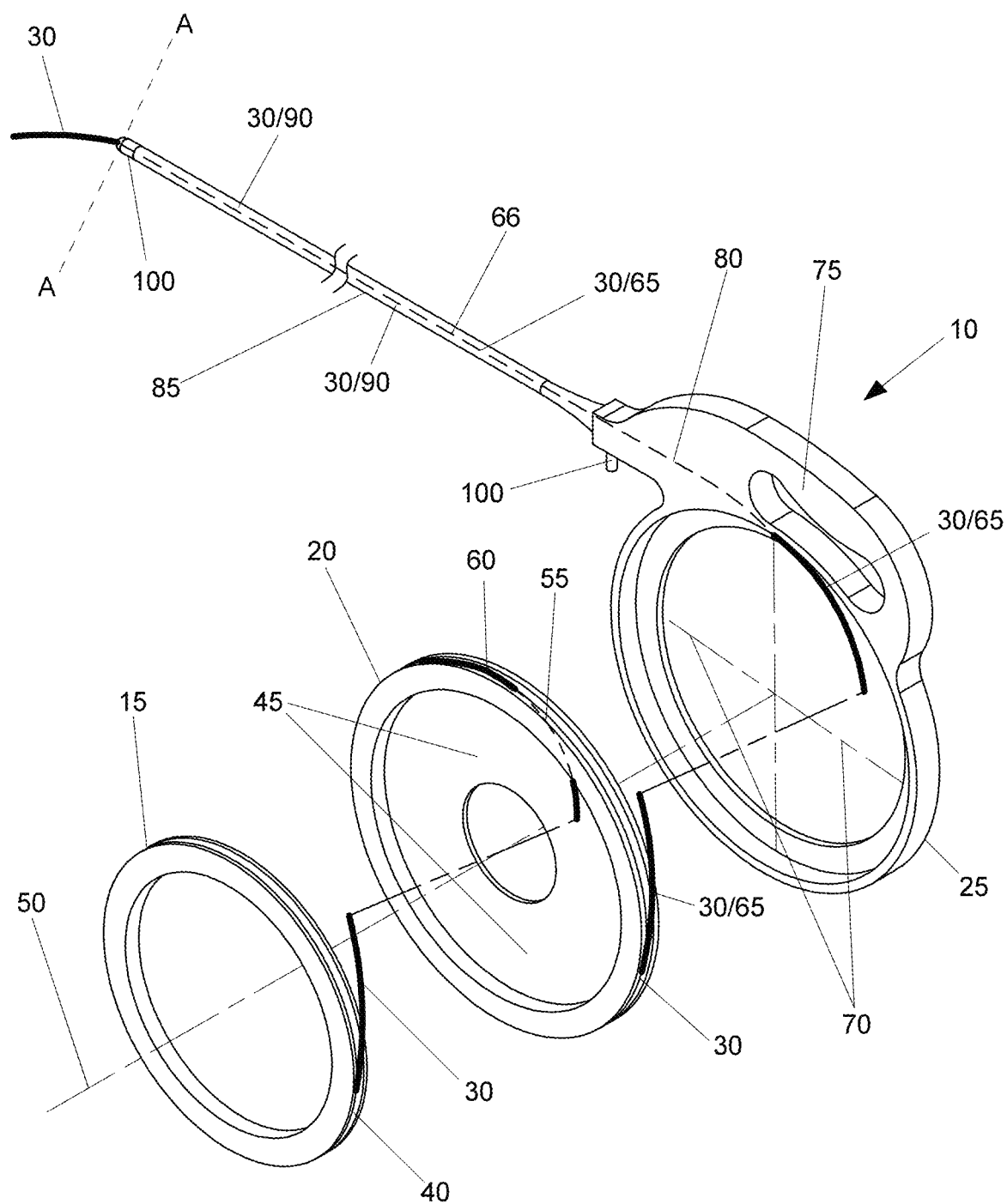
FIG. 1 illustrates an exploded view of a highly preferred apparatus of the present invention. The apparatus is not necessarily complete, however shows the components required for basic operation.

The drawings are not prepared to any particular scale or dimension and are not presented as being a completely accurate presentation of the various embodiments.

DETAILED DESCRIPTION OF THE INVENTION AND PREFERRED EMBODIMENTS THEREOF

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments, or indeed any embodiment covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

As used herein, and unless otherwise indicated, relative terms such as "proximal" and "distal" are used with the apparatus of the present invention as the reference point. Thus, the term "proximal" means close to the apparatus, and "distal" means away from the apparatus.

As used herein, the term "move", "movement" and similar terms when used with regard to a guide wire or a stent pusher, means that the distal terminal of guide wire or stent pusher is moved.

Where a structure or combination of structures or an arrangement is described to be "configured" to perform a certain function, the configuration may be in terms of any one or more of: shape, dimension, orientation, fabrication material, weight, flexibility, elasticity, deformability, resilience, rigidity, softness, roughness, smoothness, twistability, heat resistance, cold resistance, conductivity (thermal or electrical), resistance to conductivity (thermal or electrical), or any other parameter apparent to the skilled person seeking the functional outcome required. The term "configured" may also refer to non-physical parameters such as the use of computer program instructions for an item of hardware to provide a certain function.

The present invention is predicated at least in part on the inventors' discovery that the insertion of a stent (and particularly a ureteric stent) is improved where an apparatus capable of independently moving a guide wire and a stent pusher is used. In some embodiments, the apparatus is configured to move the guide wire and stent pusher together. By use of the present apparatus the practitioner inserting the stent is not required to manually manipulate the wire and stent pusher independently or together, and the process of stent insertion is therefore simplified. It is proposed that stent insertion, and particularly ureteric stent insertion, is within the ability of a non-specialist medical practitioner when the present apparatus is used.

In other embodiments the apparatus is configured to allow the guide wire and/or stent to be moved distally only a certain amount before being stopped. The practitioner is not required to use any judgement with regard to how far the guide wire and/or stent is advanced into the subject during the stent insertion procedure. Again, it is proposed that stent insertion, and particularly ureteric stent insertion, is within the ability of a non-specialist medical practitioner with use of the present apparatus.

Furthermore, it is proposed that use of the present apparatus obviates the need for imaging equipment to visualise the path of the guide wire and/or stent toward, through, or into a structure of the body to assume a required position. For example, where the stent is a ureteric stent the practitioner may advance the distal terminus of the guide wire and the stent into the renal pelvis using only simple manipulation of the present apparatus and without the need for guidance by fluoroscopy.

By the present apparatus, the guide wire and stent may be advanced together in a distal direction. As will be appreciated by the skilled artisan, the stent is moved relative to the wire using a pusher as is known in the art. The pusher is separate to the stent and functions to contact the proximal end of the stent, such that when the pusher is moved by apparatus in the distal direction the stent is also moved in the distal direction. Movement of the guide wire and stent pusher (and therefore the stent) together would be required when the practitioner is advancing the guide wire and stent to a desired location in the subject's body, such as the ureter.

By the present apparatus, movement of the guide wire relative to the stent may be provided, with the stent remaining in position (by locking the stent pusher) at the required destination in the subject's body (such as the ureter), and the guide wire is withdrawn from within the stent and back into the apparatus.

The present invention will now be more fully described by reference to the non-limiting examples shown in the drawings.

Reference is made firstly to the exploded view of FIG. 1, showing an apparatus (10) of the preferred embodiment of the invention, the apparatus comprising a first spool (15) (being a first moving means), a second spool (20) (being a second moving means) and a housing (25).

A guide wire (30) is anchored to and is wound upon the first spool (15). As will be noted, the guide wire (30) sits within a channel (40) formed in the outer circumferential edge face of the first spool (15). The distal terminus of the guide wire (30) is advanced distally upon counter-clockwise (as drawn) rotation of the first spool (15).

The first spool (15) is sized to fit inside a circular hollow (45) formed in the second spool (20) so as to allow the first spool (15) to rotate within the hollow (45) while preventing any material misalignment of the rotational axes of first (15) and second (20) spools. The guide wire (30) sits in the channel (40) and therefore does not contact the inner circumferential surface of the hollow (45).

The first (15) and second (20) spools share a common axis of rotation (50), and are able to rotate about that axis (50) relative to each other.

The guide wire (30) extends from the first spool (15) to the second spool (20) through a passage (55) formed in the second spool (20). After exiting the channel (40), the guide wire enters the passage (55) formed in the second spool (20). It will be noted that the passage (55) forms a shallow angle relative to the tangent formed with the inner circumferential edge face of the hollow (45) so as to limit bending of the guide wire (30) as it transitions out of the passage (55) and into the channel (60).

The guide wire (30) winds about the second spool (20), staying within the channel (60). At one point, the guide wire enters the lumen of a pusher (65) with which it is coaxial. The pusher (65) is anchored to the second spool (20). The distal terminus (66) of the pusher (65) is advanced distally upon counter-clockwise (as drawn) rotation of the second spool (20).

The second spool (20) sits within a space (70) of the housing (25). The pusher (65) (having the guide wire (30) contained therein) sits within the channel (60) and therefore does not contact the circumferential inner face of the space (70).

The first (15) and second (20) spools are capable of independent rotation relative to each other, and also relative to the housing (25). The housing (25) is typically held by the practitioner by a handle (75), and therefore remains stationary while the first (15) and/or second (20) spools are rotated.

The pusher (65) (containing the guide wire (30)) leaves the second spool (20) via a passage (not drawn) formed in the housing (25). The path of the passage is indicated by the dashed line (80).

From the passage (80) the pusher (65) (containing the guide wire (30)) passes into the lumen of an elongate structure in the form of a proboscis (85). The stent (90) also passes through the lumen of the proboscis (85). The proboscis (85) is drawn in truncated form. In reality, the proboscis is sufficiently long such that its distal terminus can be brought sufficiently close to the location within the body that is to receive the stent. For example, where the apparatus is for the delivery of a ureteric stent the proboscis must be sufficiently long so as to pass through the urethra until the distal end of the proboscis (85) is in the bladder.

The proboscis (85) is typically rigid or semi-rigid so as to allow the practitioner to alter the position of the proboscis (85) terminus. For example, where the apparatus is for insertion of a ureteric stent, the practitioner may alter the angle of the proboscis (85) until its terminus is directed toward the opening of the ureter to be stented. Alternatively, the proboscis (85) may be flexible, but "steerable" using mechanisms known to the skilled artisan.

Figure 2A:
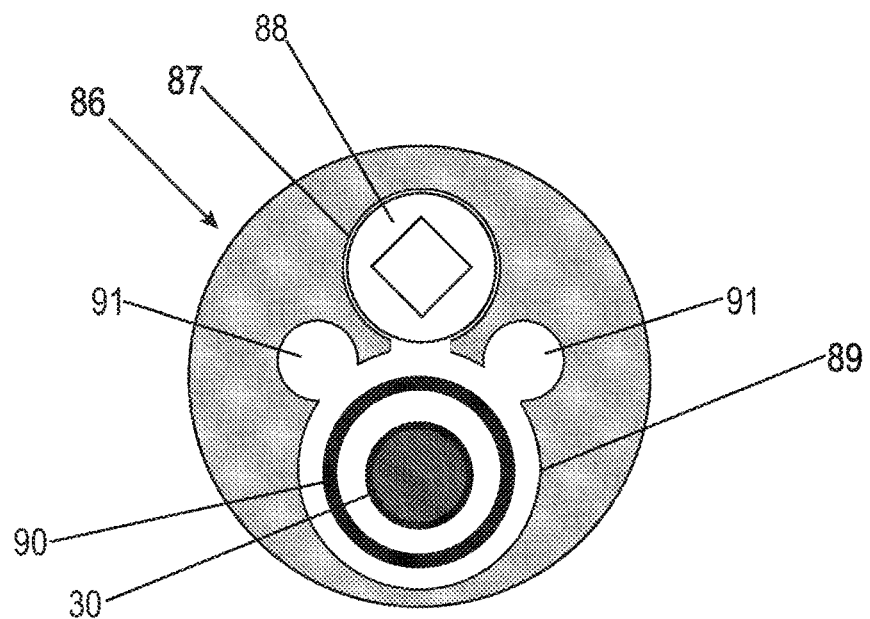
FIG. 2A illustrates the section A-A' marked on FIG. 1.
Figure 2B:
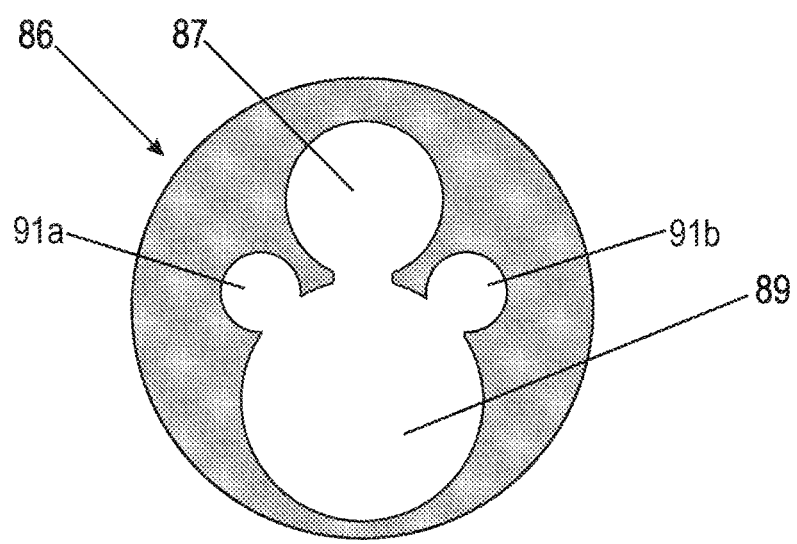
FIG. 2B is a reproduction of FIG. 2A, albeit with the internal components removed so as to more clearly show the conformation of the plug.

The proboscis (85) may comprise a terminal plug (86) which inserts snugly into the proboscis (85). Greater detail of the structure and its arrangement to other components of the apparatus is found in FIG. 2A, being a section through the line A-A' of FIG. 1. FIG. 2B shows the terminal plug (86) solus to more clearly demonstrate its structure.

The terminal plug (86) has a first axial space (87) to receive a video camera with an integrated LED light (88) allowing for visualisation of anatomical structures internal to the subject's body. Power input and signal output wires (not drawn) for the camera and light (88) pass through the rear of the terminal plug and travel through the proboscis (85) lumen to the power supply (not drawn) and electronics (not drawn) held in a cavity in the apparatus casing just behind the proximal end of the proboscis (85).

The terminal plug (86) has a second axial space (89) which accommodates, the guide wire (30), and the stent (90) (before the stent is deployed). In the section view of FIG. 2A the stent pusher (65) is not visible because it is located behind the stent (90).

The terminal plug has third and fourth axial spaces (91a, 91b) which allow passage of a flushing liquid from inside the proboscis (85) lumen to the external region proximal to the camera and light (88). As discussed below, a flushing fluid may be used to clear any suspended solid which interferes with the camera vision.

Where the apparatus is used for stenting of a ureter, the camera and light (88) are used by the practitioner to visualise the internal surfaces of the bladder and locate the opening of the ureter. Once located, the distal end of the proboscis is brought close to the ureteral opening to allow for insertion of a stent (90) held within the proboscis (85). The guide wire (30) passes through the stent (90) while within the proboscis (85).

The urine within the bladder may be cloudy, having insoluble suspended materials such as blood, casts, crystals, tissue debris, colonies of microorganisms and the like. Some means of flushing such material away from the camera (88) lens so as to improve visibility is therefore desirable. To that end the present apparatus (10) may comprise a port (100) to admit a flushing liquid into the proboscis (85) lumen. The liquid may travel under gravity or by way of some active transport means into the apparatus (10) via the port (100), and travel to the terminus of the lumen (85) where it exits primarily via the third and fourth axial spaces (91*a*, 91*b*). As will be understood, the liquid used for flushing must be biocompatible, with a sterile normal saline solution being generally preferred.

The first spool (15), second spool (20) and housing (25) are typically maintained in relative mutual position by way of some further component(s) (not drawn). For example, tabs may be provided that extend from the housing (25) and over the frontwardly presenting (as drawn) faces of the first (15) and second (20) spools. The tabs allow the rotation of the first (15) and second (20) spools, yet prevent disassociation of the apparatus (10) components (15) (20) (25). As another example, a further housing portion is provided which is complementary to the housing (25) and fitting onto the frontwardly presenting (as drawn) face of the housing (25). Again, the further housing portion does not materially interfere with rotation of the first (15) and second (20) spools.

In the preferred embodiment of the drawings, the first (15) and second (20) spools are maintained in a mutually coaxial rotating relationship by the close fitting nature of the components. Other alternatives are available, such as the use of an axle extending through the centres of the first (15) and second (20) spools.

The apparatus (10) may be configured such that the first (15) and/or second (20) spools may be rotated by hand. To facilitate hand rotation, the first (15) and/or second (20) spools may be provided with one or more holes or depressions to accept a finger or a thumb of other part of the hand. Alternatively, the first (15) and/or second (20) spools may be provided with one or more protuberances to facilitate engagement with a finger or a thumb of other part of the hand. In another alternative, a crank may be provided to turn the first (15) and/or second (20) spools.

As an alternative to hand rotation, the apparatus may comprise a small electric motor configured to rotate the first (15) and/or second (20) spools. The motor may transfer the rotatory motion of its shaft to a spool (15) (20) via a geared arrangement. The motor may be a stepper motor configured to rotate a spool (15) (20) in a controlled manner so as to limit the opportunity for damage to an anatomical structure of the body as the stent guide wire (30) and stent (90) are advanced.

The first (15) and second (20) spools may be independently rotatable, in which case no modification of the drawn embodiment would be required. Such operation is required, for example, where the guide wire (30) is withdrawn from within the stent (90).

In some circumstances it may be desirable to lock the first (15) and second (20) spools together. Such operation is required, for example, where the guide wire (30) and stent (90) are advanced into the body together so as to place the stent (90) in a required location of the body. The spools (15) (20) may be locked together by a simple U-shaped pin, the first leg of which inserts into an aperture formed in the first spool (15), the second leg of which inserts into an aperture formed in the second spool (20). The pin may be removed to allow for independent rotation of the spools (15) (20).

The apparatus (10) may be configured to prevent further rotation of the first (15) and/or second (20) spool once a predetermined length of stent guide wire (30) or stent (90) has been advanced into the body. For example, where the apparatus (10) is for the insertion of a ureteric stent the rotation of the first (15) and second (20) spools may be stopped after a length of stent guide wire (30) or stent (90) has exited the apparatus (10) that is commensurate with the expected or known length of the subject's ureter. The use of a stop mechanism of some description prevents the insertion of an excessive length of stent (90) into the ureter (or other bodily structure) thereby avoiding damage to tissue or over insertion of stent into the ureter thereby preventing the coiled end from anchoring in the bladder.

The stop mechanism may be embodied as a simple mechanical arrangement. For example a first stop member may extend from the housing (25) and a second stop member extending from a spool (15) (20), the first and second stop members colliding when a spool (15) (20) has rotated a predetermined amount. One of the stop members may be movable and lockable in place so as to adjust the length of the guide wire (30) and stent (90) that exits the apparatus (10). Such adjustment may be required according to an anatomical characteristic of the subject, such as the ureteral length.

Where the spools (15) (20) are rotated by a stepper motor, the stepper motor may function so as to limit rotation according to data input by the practitioner, thereby functioning to limit the length of guide wire (30) and stent (90) introduced into the subject. As will be appreciated, the stepper motor would require instruction by a microprocessor that is integral with the apparatus (10) or located remotely.

A further stop mechanism may be electronic in nature, and function so as to monitor the length of stent (90) or stent pusher (65) or guide wire (30) that is advanced from the apparatus (10). For example, the apparatus (10) may comprise a roller configured to output a digital or analogue signal that relates to the number of rotations through which the roller has turned. Stent (90) or stent pusher (65) or guide wire (30) that is advanced from the apparatus (10) turns the roller, and accordingly a calculation or inference may be made as to the length advanced. When the predetermined length is achieved, a locking mechanism may be actuated (such as a solenoid-actuated clamp) or an audible waning signal may be given. Again, a microcontroller would be required to effect these functions.

While the length of guide wire (30) that is extended is variable, in this preferred embodiment the proximal end of the stent (90) will extend the same distance, i.e. to the end of the proboscis (85). From its starting position, the stent (90) will be advanced the same distance irrespective of any limitation to rotation of the first spool. Thus, and by way of example only, if the guide wire (30) is advanced 30 cm, the stent (90) will advance another 30 cm (total 60 cm). As another example, if the guide wire (30) is advanced only 15 cm, the stent (90) will advance a further 45 cm (total 60 cm). In any event, at the end of the stent insertion process, the proximal terminus of the stent (90) will be level with the end of the proboscis (85).

In some embodiments, the apparatus (10) comprises means to connect the video camera in the proboscis (85) to a screen capable of displaying the video stream captured by the camera. Preferably, the display screen is provided by a mobile device such as a smart phone (Android™, iOS™ or other) or a tablet computer device (Windows™ Linux™, Android™, iOS™ or other). Accordingly, the apparatus (10) may provide an interface to connect a mobile device thereto. The interface may be a wired interface (such as a USB interface) or a wireless interface (such as a Bluetooth™ or WiFi™ interface).

Where operation of the apparatus requires a microprocessor for operation, the microprocessor may be provided by the mobile device. Data interchange between the apparatus and mobile device may be achieved by wired or wireless means as detailed supra.

Where operation of the apparatus requires data input (for example entering a ureteric length), the mobile device may function as a user interface. Where operation of the apparatus involves data output (for example the length of stent advanced by the apparatus), data interchange between the apparatus and mobile device may be achieved by wired or wireless means as detailed supra.

Use of a mobile device in combination with the present apparatus will typically require the device to have application software installed thereon. The software is typically configured to facilitate connectivity between the mobile device and the apparatus and data exchange. The application software may be further configured to retrieve subject data from a remote database allowing for identification of the subject, or details of a previously measured ureteric length, or an inferred ureteric length. The application software may be configured to allow for a new subject to be added to the remote database by the practitioner.

The practitioner may be further allowed by the application software to add information to the remote database against an entry for a new or existing subject, such as subsequent actions required including stent removal. Such entries may have a date component, such as a date for stent removal. The application software (or another item of software) may be configured to output a message on a database-recorded date such as by way of a push notification, email or SMS text message as a reminder that a subsequent action is required. While not common, the presence of a ureteric stent in a subject can be forgotten.

The application software may allow for entry of a subject contact detail in the remote database. The subject contact detail may allow for electronic contact, such as a cell phone number, an email address, or a messaging app address to list several examples. The application software (or another item of software) may dispatch educational material or appointment reminders to the device of a subject.

The application software may be configured to obtain informed consent from a client in relation to a proposed stent insertion procedure. The application software may be configured firstly to output information required for informed consent, and secondly to accept as input confirmation from the subject that he/she understands the information and consents to the stent insertion procedure. Such input/output may be by way of a graphical user interface.

The apparatus (10) may provide means for retaining the mobile device on or about the apparatus (10). Typically the retaining means is arranged such the mobile device display screen faces away from the proboscis (85) so as to be easily viewable by the practitioner as he/she advances the proboscis into the subject. Suitable retaining means includes a bracket, a pocket, a recess, a clamp, one side of a hook-and-loop attachment means, a magnet, a pressure-sensitive adhesive and the like.

Having now described the apparatus attention is now drawn to the operation thereof, described with reference to a preferred application being ureteric stent insertion.

The apparatus (10) is drawn in a state as required to commence a ureteric insertion procedure. The guide wire (30) is fully within the proboscis (85), its distal end at the distal end of the proboscis (85). The distal terminus of the stent (90) is set back from the distal terminus of the guide wire (30) by a distance, such that a distal portion of the guide wire (30) is exposed. The distance may be predetermined, and may be greater than about 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 cm. In some embodiments the distance is in the range of about 20 cm to about 30 cm.

The practitioner inserts the proboscis (85) into the subject's urethra and advances the distal end into the bladder. Under vision (i.e. with the assistance of the video camera at the distal end of the proboscis (85)) the practitioner visualises the opening of the affected ureter and manipulates the proboscis such that its distal end is adjacent to and directed toward the ureteric opening. The first (15) and second (20) spools are coupled at this juncture such that as the practitioner rotates the first spool (15) the second (20) spool is rotated in the same direction to advance firstly the exposed distal portion of the guide wire (30) into the ureter and the stent (90) towards the end of the proboscis (85). Rotation of the first (15) and second (20) spools is continued such that the stent (90) and the guide wire (30) are together advanced into the ureter until the distal end of the guide wire (30) is located in the renal pelvis. Proper location may be inferred according to an expected ureteric length for the subject, or alternatively by way of an imaging technique such as fluoroscopy or ultrasound.

In some embodiments the apparatus comprises a stop which prevents further rotation of the first spool (15) so as to prevent further advancement of the guide wire (30) beyond a predetermined distance. Generally, the predetermined distance is approximately or exactly the known or inferred ureteric length. The second spool (20) is uncoupled from the first spool (15) and is therefore independently rotatable so as to push the stent (90) along the guide wire (30). The rotation of the first spool is prevented by the stop, and so it is only the stent (90) which is advanced at this stage. The rotation of the second spool beyond the predetermined distance (corresponding to the proximal end of the stent being level with the end of the lumen of the proboscis (85)) is prevented by a stop. At that point the stent (90) is properly located; i.e. the distal end of the stent (90) in the renal pelvis, and the proximal end of the stent (90) in the bladder.

With the stent (90) properly located, the guide wire (30) is withdrawn from within the stent (90) by rotation of the first spool (15) in the opposite direction, while the second spool (20) remains stationary. In one embodiment, the first (15) and second (20) spools are automatically uncoupled leaving the first spool (15) rotatable while the second spool is stationary. Thus, the guide wire is removed, leaving the stent in place in the ureter.

Upon withdrawal of the guide wire (30) the distal end of the stent (90) assumes its biased coiled conformation thereby securing it within the renal pelvis. Once the guide wire (30) is fully withdrawn from the stent (90) the proximal end of the stent (90) also assumes its biased coiled conformation thereby securing it in place within the bladder.

The guide wire (30) is withdrawn until its distal end is within the proboscis (85). The practitioner then withdraws the proboscis (85) through the urethra and clear of the subject's body.

Figure 3A:
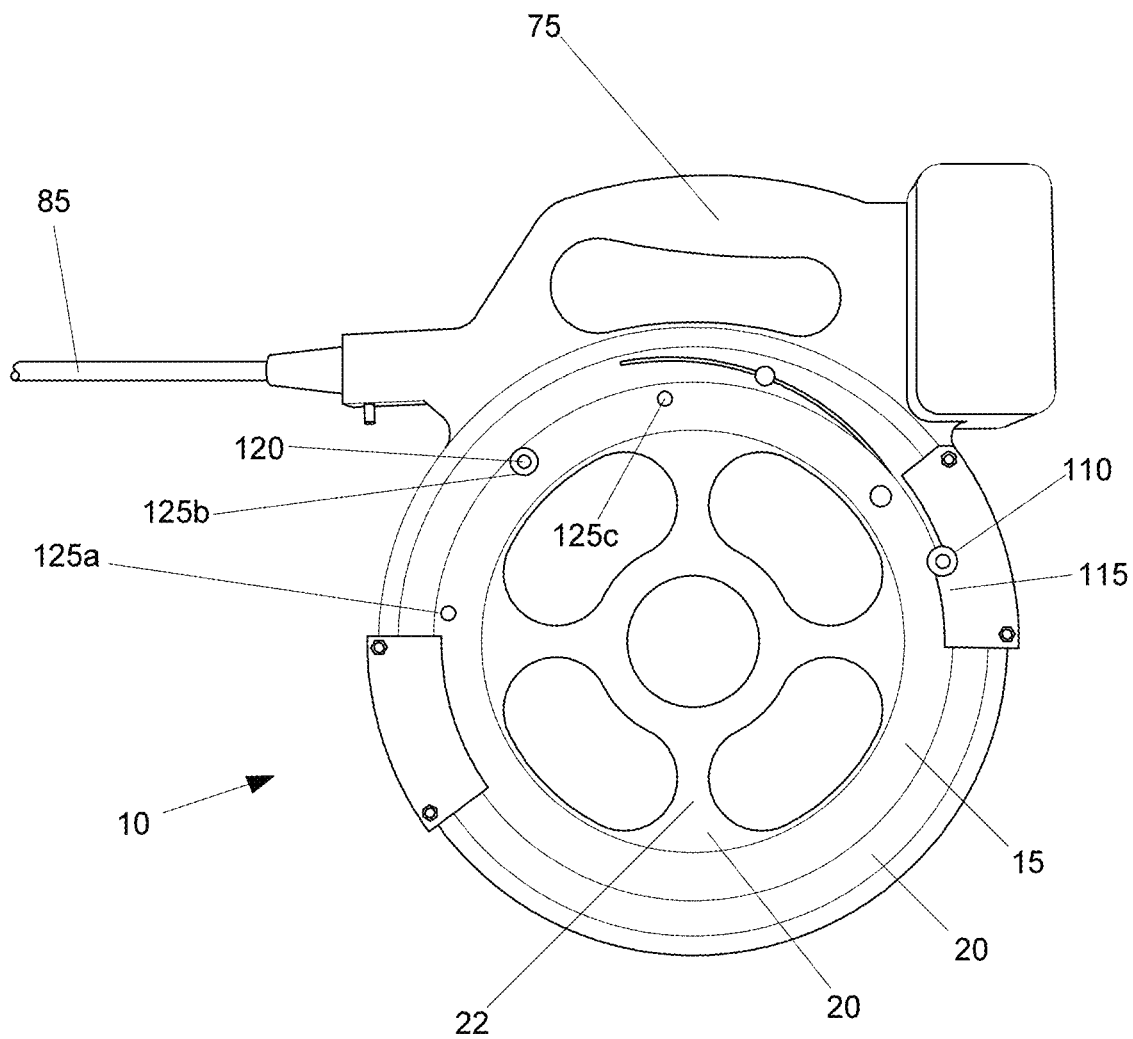
FIG. 3A illustrates a highly preferred apparatus of the present invention in lateral view.
Figure 3B:
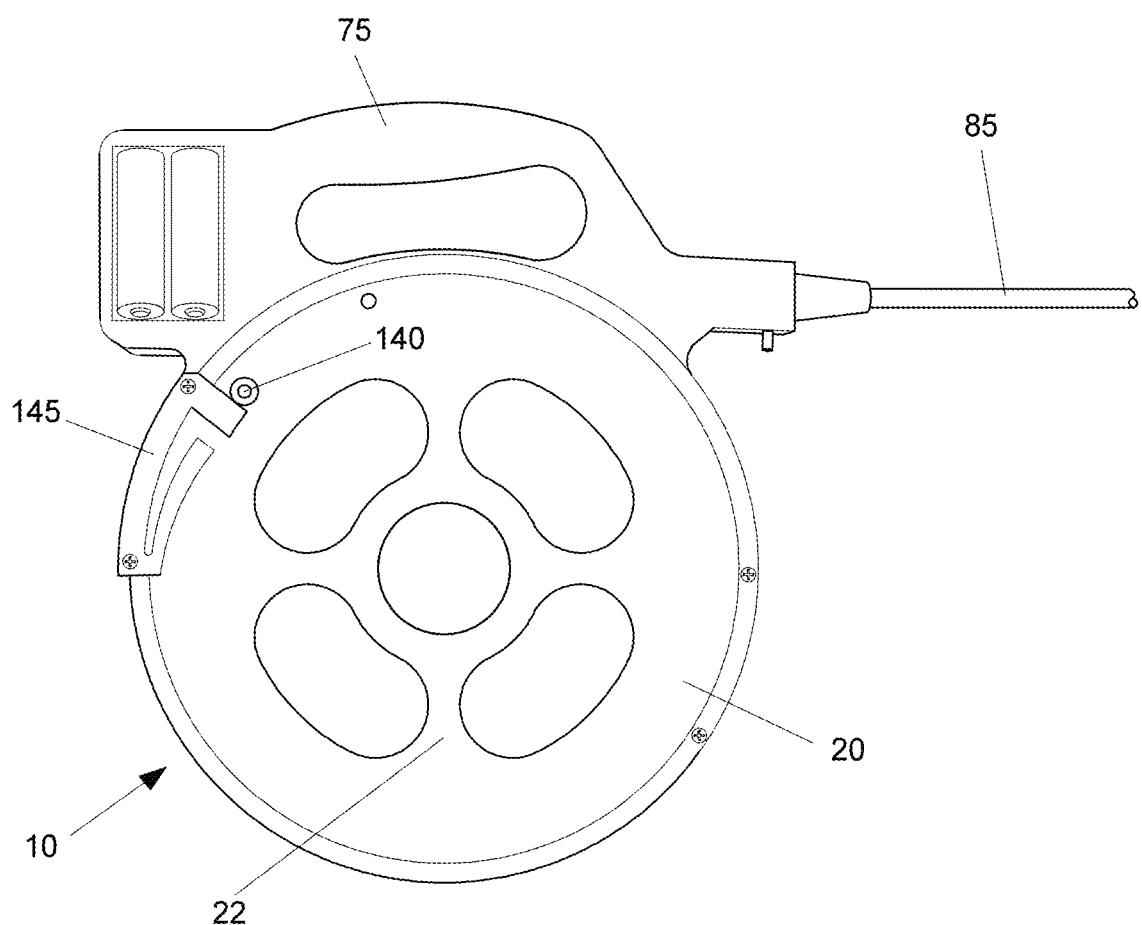
FIG. 3B is a reverse view of the embodiment of FIG. 3A.
Figure 3C:
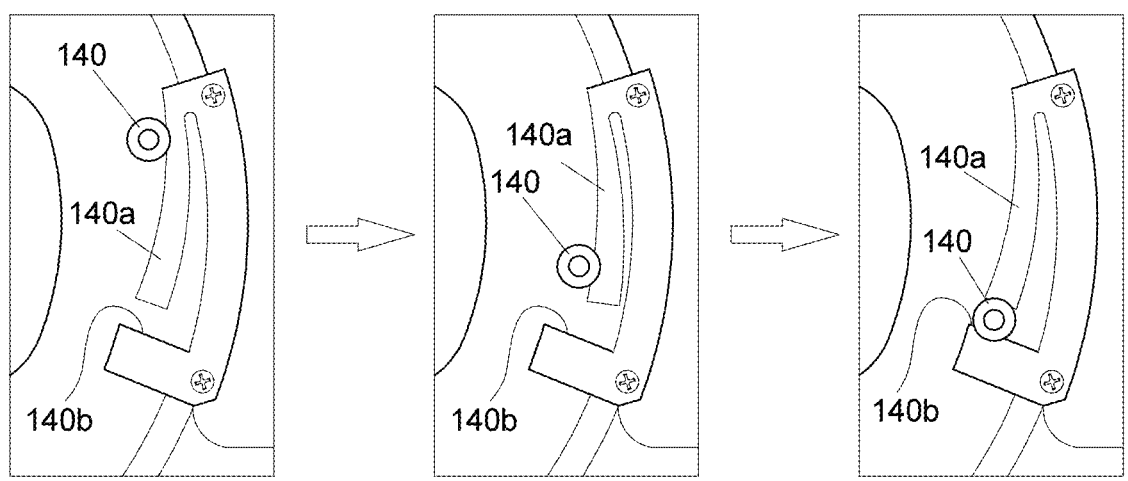
FIG. 3C shows three sequential illustrations demonstrating operation of the latching mechanism.

Turning now to a further consideration of stop mechanisms configured to prevent over rotation of the spools, reference is made to the embodiment of FIG. 3A and FIG. 3B.

A first stop mechanism is provided by the permanently mounted pin (110) extending from the first spool (15). As shown in FIG. 3A, the pin (110) abuts the stop member (115) to prevent any further clockwise rotation of the first spool (15). This first stop mechanism allows for the guide wire (30) to be withdrawn into the proboscis (85), but not so far that the end of the guide wire (30) is withdrawn through the proximal end of the proboscis (85) and into the housing (25). If the end of the guide wire (30) were to be inadvertently withdrawn from the proboscis, it may be impossible to reintroduce it back into the proboscis (85) lumen.

A second stop mechanism is provided for the first spool (15). This second stop mechanism allows for the selection of one of three different stop settings based on the estimated ureteric length of the subject. Generally, ureteric length is approximately proportional to subject height, and accordingly the three settings are referred to as "short", "medium" and "tall". A setting is selected by inserting a pin (120) into one of three apertures (125a, 125b, 125c) formed in the first spool (15). Aperture (125a) is selected where the subject is short, aperture (125b) is selected where the subject is medium height, and aperture (125c) is selected where the subject is tall. In FIG. 3A the pin (120) is inserted into aperture (125b) because the subject is of medium height.

Of course, more than three stop settings may be provided, such as 4, 5, 6, 7, 8, 9, 10 or more. In some embodiments, each stop settings is marked with a numerical indicator. For example, multiple settings at interval lengths may be used (such as 20 cm, 22 cm, 24 cm, 28 cm, 30 cm etc) to reflect the expected or predicted ureteric length. Alternatively, height ranges may be used to indicate stop settings, such as 150 cm-164 cm, 165 cm to 179 cm and 180 to 184 cm.

As the first spool (15) is rotated counter-clockwise so as to advance the guide wire (30) into the ureter, the pin (120) moves with the first spool (15) until it contacts the stop member (115). At that point, the first spool (15) can be rotated no further, thereby preventing an excessive length of guide wire (30) being advanced into the ureter. As will be appreciated, if the pin (120) were placed in aperture (125c) the first spool (15) could be rotated further so as to allow for a further length of guide wire (30) to be advanced into the ureter, as would be required for a taller subject having a longer ureter. Similarly, a shorter length of guide wire can only be advanced where the pin (120) is set for a shorter subject.

Figure 4A:
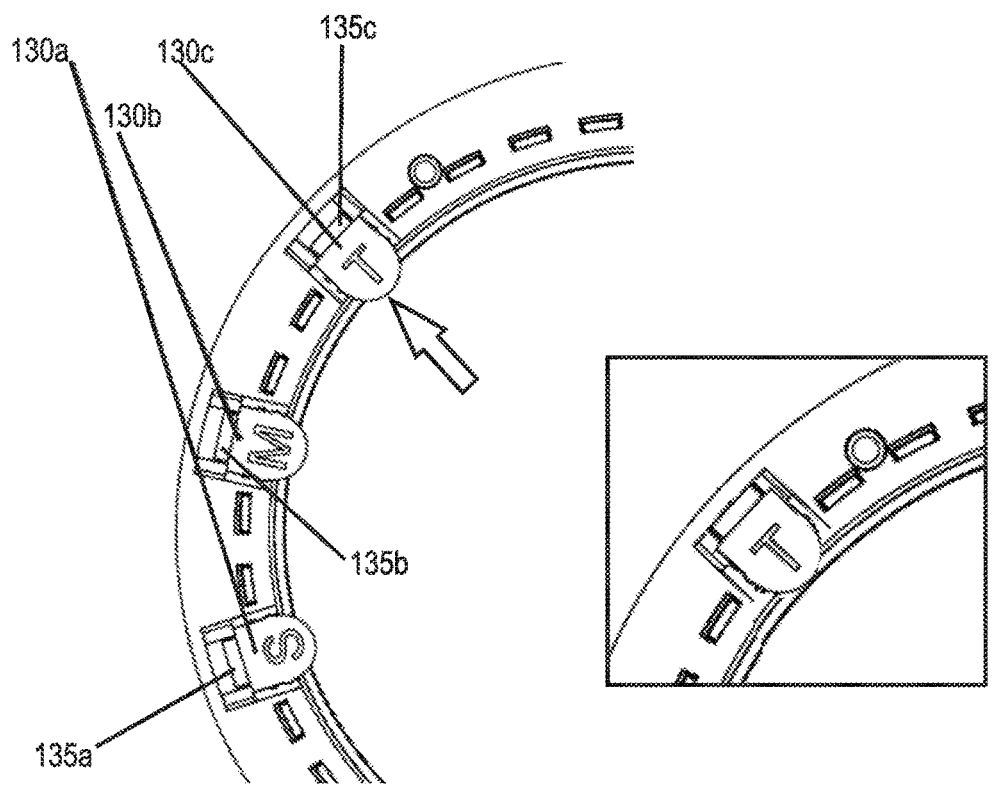
FIG. 4A illustrates radially movable tabs, each in the disengaged position so as to be incapable of contacting a stop member. The inset shows the tab "T" moved into an engaged position so be capable of contacting a stop member.
Figure 4B:
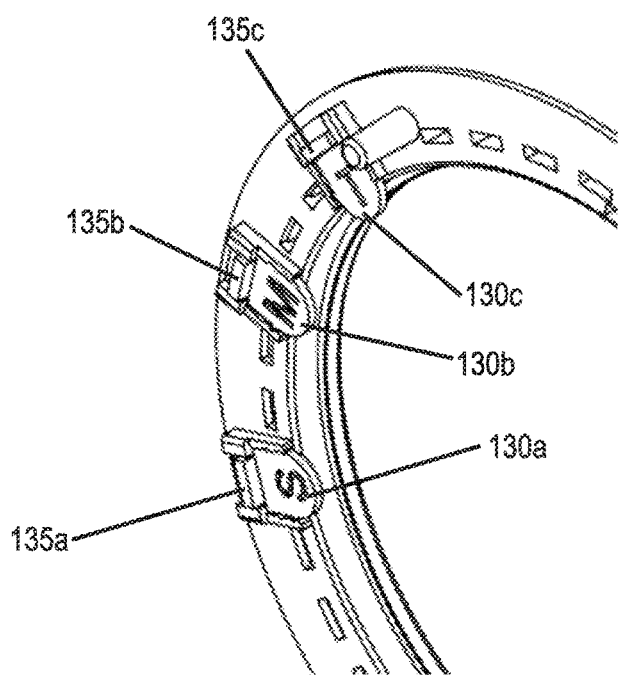
FIG. 4B illustrates the radially movable tabs of FIG. 4A in perspective view so as to more clearly show the orthogonally extending wall of each.

An alternative to the pin and aperture arrangement detailed above, is shown in FIG. 4A and FIG. 4B. A series of sliding tabs (130a, 130b, 130c) tabs are mounted on the first spool in the same circumferential position as for the apertures (125a, 125b and 125c). A tab is selected by sliding it radially outwardly, as shown by the superimposed arrow for the tab (130c) ("T"=tall).

It will be note more readily from FIG. 4B that each tab (130a, 130b, 130c) has a short wall (135a, 135b, 135c) extending orthogonally therefrom. When a tab (130a, 130b, 130c) is not selected, the wall (135a, 135b, 135c) is positioned as drawn; i.e. distal to the first spool (15) outer edge. When a tab (130a, 130b, or 130c) is selected, the wall (135a, 135b, or 135c) is moved proximal to the first spool (15) perimeter, as shown in the inset to FIG. 4A. In the position shown in the inset, the wall (135a, 135b, or 135c) is able to contact a stop member (not drawn) extending from the apparatus housing, thereby preventing further rotation. When a tab (130a, 130b, 130c0 is in the original position (i.e. distal to the spool (15) outer edge) no contact with the stop member is possible and therefore further rotation is allowed.

Of course, alternative functioning would allow for a tab to be selected by sliding radially inwardly so long as the position of the step member is appropriately located.

Turning to FIG. 3B, reference is made to the latching mechanism, comprising pin (140) extending from the second spool (20) and pin lock (145) on the reverse side of the apparatus (10). This latching mechanism catches and locks the second spool (20) to prevent rotation in both directions. This locking allows the first spool (15) to rotate in the reverse direction so as to withdraw the guide wire (30), while leaving the second spool (20) stationary and the stent (90) and stent pusher (65) in place.

The embodiment of FIG. 3A and FIG. 3B will now be described by reference to the normal course of operation by a practitioner.

As described above, the proboscis (85) is inserted into the bladder via the urethra. Once the distal portion of the guide wire (30) is inserted into the ureteral opening, the practitioner grips the second spool (20) about the spokes (one marked 22). The second spool (20) is rotated counter-clockwise by the practitioner. Simple frictional forces couple the first (15) and second (20) spools causing the first spool (15) to rotate along with the second spool (20). Given that both spools (15, 20) are rotating, the guide wire (30), stent pusher (65) and stent (90) are all advanced out of the proboscis (85) together at the same rate into the ureter. When the guide wire (30) has been extended as far as possible (as governed by any stop mechanism preventing further rotation of the first spool (15)), further rotation of the second spool (20) only is still permitted because the frictional forces between the spools (15, 20) are overcome by the practitioner continuing to turn the second spool (20). The further rotation causes the stent pusher (65) to push a short portion of the distal end of the stent (90) over the distal end of the guide wire (30).

Rotation of the second spool (20) is eventually stopped by the latching mechanism. Specifically, the pin (140) deforms the flexible portion (140a) of the pin lock (140) as the second spool (20) is rotated. The rotation is stopped by the pin (140) contacting the surface (140b), and at that time the flexible portion (140a) rebounds to its original position thereby trapping the pin (140). With the second spool (20) now immobilised, the practitioner can rotate the first spool (15) in the reverse direction so as to withdraw the guide wire (30) while leaving the stent (90) and stent pusher (65) in place. Withdrawal of the guide wire (30) allows the stent (90) to assume the coiled conformations at each end.

The embodiments of the invention as described thus far do not require the first and second spools to rotate more than one revolution in order to move the guide wire or stent pusher the required distances (proximally or distally). In an alternative embodiment of the invention, one or both of the spools may be operable such that that multiple revolutions are required. Typically both spools are operable such that that multiple revolutions are required. In this alternative embodiment the radii of the spools may be considerably smaller than those of apparatus as drawn herein.

Each of the spools are generally barrel-shaped, arranged in a nested manner with one spool sitting inside the other. The spools are in mutual threaded engagement such that one can turn independently of the other. To facilitate manual rotation, each spool may have gripping formations allowing for engagement of fingers therewith. The gripping formations may further allow for one spool to be held stationary while the other is rotated.

As an alternative to manual operation, one or both spools may be rotated by a motor (such as a stepper motor) under the control of a processor having access to software instructions, and in which case the spools may be toothed or grooved for example to allow them to be driven by the motor. The software instructions may prevent either spool from being over rotated, thereby negating the need for any physical stop arrangement.

Each of the spools may comprise two start helix grooves, as compared to the drawn embodiment which has a single groove on each spool. The spools are arranged in a nested manner with the inner spool being grooved to accommodate the guide wire, and the outer spool grooved to accommodate the stent and the stent pusher. The second start helix groove on each spool may be in the form of ACME thread or similar to provide the lateral force required to transfer the wire from the inner spool to the outer spool, and also to transfer the guide wire and stent and stent pusher to the proboscis.

As will be appreciated, some or most or all components of the present apparatus may be fabricated from medical grade materials that are also capable of sterilization. The hosing of the device mat be generally sealed, and not openable by the user. Typically, the apparatus is intended for single use only.

The present invention has been detailed mainly by reference to an apparatus for the insertion of a ureteric stent. The invention is not to be taken as limited to apparatus and methods on for that application. Given the benefit of the present specification the skilled artisan will routinely conceive of other applications, and furthermore will conceive of modifications to the drawn embodiment and description thereof that may facilitate other applications.

Various features of the invention are described by reference to the drawings, and particularly to the numbered components of the drawings. It is the intention that any component of the drawings may be taken away from the context of the drawn embodiment and used in combination with an embodiment that is different to that drawn. For example, a feature of the drawn embodiment may be combined with any feature defined in the Summary of Invention section, the Detailed Description section, or the Claims herein.

Those skilled in the art will appreciate that the invention described herein is susceptible to further variations and modifications other than those specifically described. It is understood that the invention comprises all such variations and modifications which fall within the spirit and scope of the present invention.

While the invention has been disclosed in connection with the preferred embodiments shown and described in detail, various modifications and improvements thereon will become readily apparent to those skilled in the art.

Accordingly, the spirit and scope of the present invention is not to be limited by the foregoing examples, but is to be understood in the broadest sense allowable by law.

The invention claimed is:

1. An apparatus for inserting a stent into a bodily structure of a subject, the apparatus comprising:
    a housing;
    a stent guide wire having a distal terminus;
    a first rotatable winder about which a portion of the stent guide wire is wound, the first winder being rotatable relative to the housing to move the distal terminus of the stent guide wire distally toward or along a bodily structure of a subject;
    a stent pusher disposed about another portion of the stent guide wire, the stent pusher having a distal terminus; and
    a second rotatable winder about which a portion of the stent pusher is wound, the second winder being rotatable relative to the housing to advance the distal terminus of the stent pusher distally;
    wherein the apparatus is configured for rotation of the second winder relative to the first winder to advance the distal terminus of the stent pusher distally relative to the stent guide wire.

2. The apparatus of claim 1, wherein the first winder and the second winder are also configured to be coupled together such that the stent guide wire and the stent pusher are movable together.

3. The apparatus of claim 1, comprising a lock mechanism configured to alternately lock and unlock the first and second winders to and from each other such that alternately (i) the stent pusher is movable relative to the stent guide wire, and (ii) the stent guide wire and the stent pusher are movable together.

4. The apparatus of claim 1, wherein the first and second winders are independently lockable so as to prevent movement in a direction.

5. The apparatus of claim 1, wherein the first and second winders each have a radially outwardly facing channel surrounding an associated rotational axis, and the stent guide wire and stent pusher are wound onto the respective outwardly facing channel.

6. The apparatus of claim 1, wherein the first and second winders are each a structure having a circular cross-section and stent guide wire and stent pusher are wound onto a circumferential edge face of the respective structures.

7. The apparatus of claim 6, wherein each structure having a circular cross-section is a wheel, a spool, a reel, a bobbin, a drum, or a functional equivalent thereof.

8. The apparatus of claim 1, wherein the first and second winders are arranged in a nested manner.

9. The apparatus of claim 8, wherein the guide wire passes through a passage formed in the second winder.

10. The apparatus of claim 9, wherein the guide wire enters a lumen of the stent pusher.

11. The apparatus of claim 1, wherein rotational axes of the first and second winders are coincident.

12. The apparatus of claim 1, configured such that the first and second winders are movable by hand or by a mechanism comprising a motor, a biasing means, or a spring.

13. The apparatus of claim 1, configured to limit an insertion distance of the stent guide wire and/or the stent pusher.

14. The apparatus of claim 13, further including a stop to limit rotation of the first winder to thereby limit the insertion distance of the stent guide wire by the first winder.

15. The apparatus of claim 14, wherein the stop is adjustably located.

16. The apparatus of claim 14, wherein the first winder and the second winder are frictionally coupled together, until the first winder meets the stop, whereupon the first winder and the second winder are uncoupled.

17. The apparatus of claim 13, comprising a latching mechanism configured to limit the insertion distance of the stent pusher to limit the rotation of the second winder.

18. The apparatus of claim 17, wherein the latching mechanism locks the second winder to prevent rotation in both directions.

19. The apparatus of claim 18, wherein the first winder is rotatable to withdraw the guide wire while the second winder is locked.

20. The apparatus of claim 1, wherein the housing provides a handle or a gripping surface.

21. An apparatus for inserting a stent into a bodily structure of a subject, the apparatus comprising:
    a housing;

a stent guide wire having a distal terminus, at least a portion of the stent guide wire being wound on a first movable structure within the housing;

a stent pusher disposed about another portion of the stent guide wire, the stent pusher having a distal terminus, at least a portion of the stent pusher being wound on a second movable structure within the housing;

wherein the apparatus is configured to advance the stent pusher distally relative to the stent guide wire to push the stent along the stent guide wire, wherein the second movable structure is movable relative to the first movable structure for unwinding of the stent pusher from the second movable structure.

22. The apparatus as claimed in claim 21, wherein the first movable structure and the second movable structure are configured to be coupled together such that the stent guide wire and the stent pusher are movable together such that the distal termini of the stent guide wire and the stent pusher advance distally.

23. The apparatus of claim 21, wherein the apparatus is configured for movement of the first movable structure relative to the second movable structure to withdraw the stent guide wire.

24. The apparatus as claimed in claim 21, wherein a stent is provided within the housing, the stent guide wire being at least partially disposed within the stent.

25. The apparatus as claimed in claim 24, wherein the housing further provides a proboscis and the stent is received within the proboscis and the distal end of the stent pusher is disposed within the proboscis.

26. A method for inserting a stent into a bodily structure of a subject, the method comprising:

providing the apparatus of claim 1 with the stent;

introducing the apparatus and stent into the body of a subject;

operating the first winder and the second winder together, to advance the stent guide wire and the stent pusher distally, until the distal terminus of the stent guide wire is located within or about a bodily structure of the subject in need of stenting; and subsequently operating the second winder to move the distal terminus of the stent pusher relative to the stent guide wire to an end position so as to push the stent until a distal terminus thereof is located within or about the bodily structure in need of stenting.

27. The method as claimed in claim 26, wherein the first winder is stopped by a stop to limit further rotation of the first winder to limit further advancement of the stent guide wire.

28. The method as claimed in claim 26, wherein the second winder is latched upon reaching the end position.

29. The method as claimed in claim 28, further including operating the first winder in the opposite direction to withdraw the stent guide wire.

* * * * *